United States Patent [19]

Vaillancourt

[11] Patent Number: 4,998,927
[45] Date of Patent: Mar. 12, 1991

[54] CONNECTOR

[76] Inventor: Vincent L. Vaillancourt, 14 Bunyan Dr., Livingston, N.J.

[21] Appl. No.: 395,762

[22] Filed: Aug. 18, 1989

[51] Int. Cl.⁵ ............................................ A61M 25/00
[52] U.S. Cl. .................................... 604/283; 604/411; 604/905
[58] Field of Search ................ 604/283, 284, 905, 411

[56] References Cited

U.S. PATENT DOCUMENTS

| | | | |
|---|---|---|---|
| 4,161,949 | 7/1979 | Thanawalla | 604/905 X |
| 4,318,401 | 3/1982 | Zimmerman | 604/284 X |
| 4,617,012 | 10/1986 | Vaillancourt | 604/283 X |
| 4,781,702 | 11/1988 | Herrli | 604/284 |
| 4,798,605 | 1/1989 | Steiner et al. | 604/411 |

Primary Examiner—John D. Yasko
Attorney, Agent, or Firm—Kenyon & Kenyon

[57] ABSTRACT

The connector is constructed with a housing in which a hollow needle is disposed in a sealed condition. A rubber septum is spaced from the needle to close off a chamber with a female adaptor. The needle is able to pierce through the septum to communicate with the chamber within the female adaptor. A suitable male luer connector or the like can be inserted into the female adaptor in order to supply a medicament for infusion into a fluid transfer line via the hollow needle, a collapsible sleeve is used to seal off the needle while permitting movement of the needle into the septum.

30 Claims, 3 Drawing Sheets

CONNECTOR

This invention relates to a connector. More specifically, this invention relates to a medical connector.

As is known, needles are routinely used in hospitals for the transfer of medicaments to patients under aseptic conditions. For example, in some cases, it has been quite common for needles to be attached to a luer connector of an IV bag and to be inserted into Y sites The advantages provided by this include the transfer of a medicament under aseptic conditions and, upon removal of the needle, a self sealing system to maintain a IV line sterile.

A second system which is also quite common is for a catheter to be inserted into a patient with an intermittent injection port connected to the catheter In this system, the intermittent port contains a rubber septum through which a needle may pass for the infusion of medicaments. As in the above case, the transfer of medicaments can be accomplished aseptically.

However, in these and other types of fluid transfers, the exposed needle can readily cut a user and, possibly lead to blood contamination with potentially life threatening results.

In the past, various types of structures have been proposed to avoid needle sticks from needles, for example, as described in U.S. Pat. No. 4,752,292. In this case, it has been proposed to mount the needle within a cap member so that the needle does not project beyond the cap member. In this case, the cap member is, in turn, formed so as to be mounted on a connector having a seal which can be pierced by the needle. However, such medical connectors are rather cumbersome in construction and in use.

Accordingly, it is an object of the invention to minimize the possibility of a needle puncture in the application of medicaments to a patient.

It is another object of the invention to provide a connector of relatively simple construction which can be used in the aseptic transfer of medicaments to a bedridden patient.

It is another object of the invention to provide a connector which is simple to use for the periodic delivery of a medicament to a patient.

It is another object of the invention to provide a connector which can be constructed at a minimum of cost.

Briefly, the connector is constructed with a housing in which a hollow needle is mounted in a self-contained recessed manner. In addition, a rubber septum is disposed in the housing in facing relation to a distal end of the needle while an adaptor is provided which extends coaxially of the needle on a side of the septum opposite the needle in order to define an internal chamber. The needle and the septum are initially disposed in opposed spaced relation relative to each other while the adaptor is movable into the connector in order to permit the needle to pierce through the septum into communication with the chamber of the adaptor.

In one embodiment, the connector is constructed for mounting between two tubes of an IV line. In this case, the housing has a hollow cylindrical portion defining a flow path for fluid and is adapted to receive tubing at opposite ends. In addition, a female adaptor is provided with extends radially of and in communication with the flow path in the cylindrical portion while the rubber septum is disposed in the adaptor to separate the internal chamber of the adaptor from the flow path in the cylindrical portion of the housing. A collapsible means in the form of a cylindrically shaped structure is mounted on the housing with an end wall secured to the needle and a cylindrical collapsible wall spaced concentrically about the needle and secured to the housing. Upon collapsing of the wall from an extended position with the needle spaced from the septum to a collapsed position, the needle pierces the septum and extends into the chamber of the adapter for conveying fluid therefrom. In addition, the needle is provided with at least one aperture at an intermediate point which opens into the flow path of the cylindrical portion of the housing so that the fluid conveyed from the adapter chamber is directed into the flow path of a fluid passing through the tubing connected to the housing.

When in use, a male adaptor of a fluid supply is inserted into the female adaptor. In this way, fluid, such as a medicine, contained in the fluid supply can be delivered to the chamber of the female adaptor under a slight pressure. Next, the collapsible cylinder to which the hollow needle is connected is collapsed to cause the hollow needle to pierce the septum. The fluid in the female adaptor chamber is then able to flow through the hollow needle and into the main flow path via the aperture in the side wall of the needle.

When delivery of the fluid is to cease, the collapsed cylinder is expanded, thus, withdrawing the needle from within the septum. In this respect, the septum is self-sealing so that upon withdrawal of the needle, the septum seals on itself so that the chamber within the adapter and the main flow path are sealed from each other. Thereafter, the male adaptor of the fluid supply can be removed. At this time, a cap can be placed over the female adaptor to maintain a sterile condition.

In another embodiment, the connector has a housing with a male luer connection at one end which defines a flow path for fluid. In this case, the hollow needle is mounted in the housing coaxially of the male luer connection and is provided with a proximal end opening into the flow path of the connection. In addition, a female adaptor is slidably mounted in the housing coaxially of the needle to define an internal chamber while a rubber septum is disposed in sealed relation between the female adapter and the needle. In this case, a collapsible sleeve means is disposed about the needle between the housing and the adapter in order to seal the space about the needle and to permit the needle to pierce through the septum into communication with the adaptor during movement of the adaptor into the housing. In this way, fluid can be conveyed from the adapter chamber through the hollow needle into the flow path of the male luer connection. In this embodiment, the collapsible means may be formed by a collapsible cylindrical wall while being integral with the septum.

This latter embodiment can be used with a Y-site. In this respect, the male luer connection can be inserted into a branch of a Y-site. In this condition, a male adaptor of a fluid supply means can be inserted into the female adaptor in a sealed relationship. Thereafter, the male adaptor is pushed into the female adaptor such that the female adaptor moves into the housing of the connector to cause the hollow needle to pierce the septum thereby communicating the fluid within the female adaptor with the interior of the Y-site branch. Withdrawal of the female adaptor to a retracted position within the housing causes the needle to withdraw from the septum, thereby stopping further flow of fluid into the branch of the Y-site.

As a variant, the collapsible sleeve means may be disposed between the housing and the adapter to form a seal therebetween. In this embodiment, the sleeve means is expanded from a normally collapsed position to an expanded position when the adaptor is moved into the housing. In addition, in both cases, a pair of seal rings are integrally formed on the septum to sealingly engage with the housing to complete a double seal arrangement.

In still another embodiment, the connector may be constructed to be placed in a fluid supply line. In this embodiment, the connector has a tube defining a fluid path for fluid while also having a hollow stub extending radially of and in communication with the flow path. In addition, a holder is mounted in the stub with a needle extending through the holder so that a proximal end of the needle is in communication with the flow path. A housing is also mounted on the stub concentrically of the holder while a female adaptor is mounted in the housing to extend coaxially of the needle. A rubber septum is also disposed in sealed relation between the adaptor and the needle. As above, a collapsible means is disposed about the needle between the holder and the adaptor so as to aaseptically seal off the needle in a position of non-use and to permit the needle to pierce through the septum during movement of the adaptor towards the needle in order to convey fluid from the chamber of the adaptor into the flow path of the tube.

In this embodiment, the collapsible means is integral with the septum and has an end wall opposite the septum to define a closed chamber within which the distal end of the needle is positioned. This connector can be used in a manner similar to the above.

These and other objects and advantages of the invention will become more apparent from the following detailed description taken in conjunction with the accompanying drawings wherein.

Figure 1:
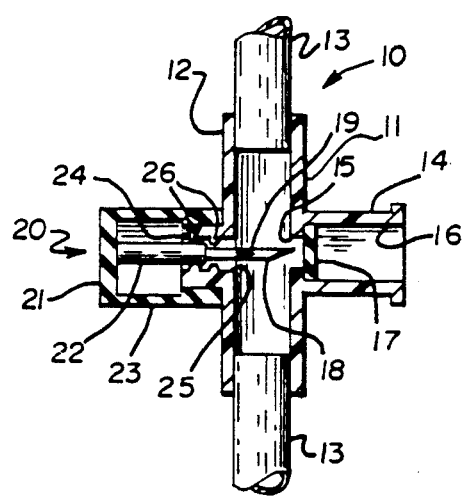
FIG. 1 illustrates a cross sectional view of a connector disposed within an IV line in accordance with the invention.

Referring to FIG. 1, the connector 10 has a plastic housing 11 provided with a hollow cylindrical portion 12 to define a flow path for fluid which is adapted at opposite ends to receive tubing 13, for example, of an IV line extending from a fluid supply (not shown) to a bed-ridden patient (not shown).

In addition, the connector 10 has a female adaptor 14 extending radially of and in communication with the flow path in the cylindrical portion 12 via an opening 15. The adaptor 14 is integral with the housing 12 and serves to define an internal chamber 16.

A rubber septum 17 is disposed in the adaptor 14 in order to separate the chamber 16 from the flow path in the cylindrical portion 12. This septum 17 may be secured in place in any suitable fashion.

A hollow metal needle 18 is mounted in the housing 11 in spaced coaxial relation to the septum 17. In this respect, the hollow needle 18 has a sharp distal end capable of piercing through the rubber septum 17 into the chamber 16 of the adaptor 14. In addition, the needle 18 has an aperture 19 in the side wall opening into the cylindrical portion 12.

Figure 2:
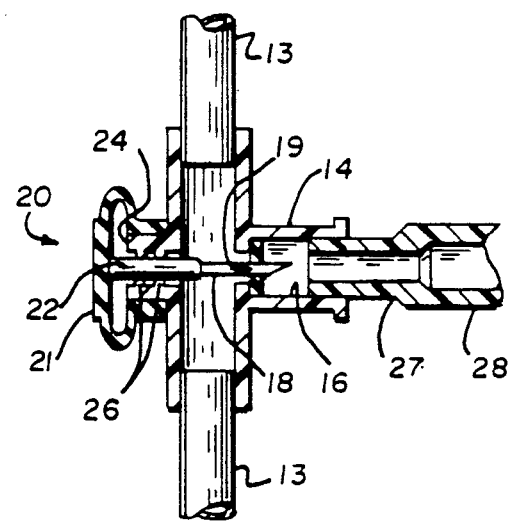
FIG. 2 illustrates a cross sectional view of the connector in a collapsed state of the collapsible means.

A collapsible means 20 is disposed on the housing 11 and is secured to the needle 18 for movement between an extended position with the needle 18 spaced from the septum 17 and a collapsed position, as illustrated in FIG. 2, with the needle 18 piercing the septum 17 and extending into the chamber 6 for conveying fluid from the chamber 16 into the flow path defined by the cylindrical portion 12 of the housing 11. The collapsible means 20 includes an end wall 21 which is secured to a proximal end of the needle 18, for example, via a sleeve-like holder 22 as well as a collapsible cylindrical wall 23 which is spaced concentrically about the needle 18. Alternatively, the wall 23 may be accordion-shaped. This collapsible wall 23 is secured to a stub 24 extending radially from the housing 11.

As indicated, the stub 24 defines an opening 25 through which the needle 18 projects. The stub 24 is also provided with a sealing means, for example, in the form of two annular ribs 26 to seal against the sleeve 22 in which the needle 18 is mounted.

In order to use the connector 10, the cylindrical portion 12 of the housing 11 is positioned between two lengths of tubing 12 of an IV line to provide for a continuity in the flow of fluid between the two lengths of tubing 13. This connection may be formed in any suitable manner to maintain a sterile connection.

In order to introduce a medicament into the IV line, a male adaptor 27 which is connected with a suitable fluid supply means, such as a syringe 28, is inserted into the female adaptor 14. The fluid within the supply means 28 is then introduced under a slight pressure into the chamber 16 of the adapter 14. Next, the collapsible means 20 is collapsed into the collapsed position shown in FIG. 2 so that the needle 18 pierces the septum 17 bringing the distal end of the needle 18 into the chamber 16. In this position, the needle 18 is able to convey the fluid in the chamber 16 through the aperture 19 in the side wall into the flow path of the fluid in the IV line.

After a suitable amount of medicament has been introduced into the IV line, the collapsed wall 23 may be pinched so as to flex back into the extended position indicated in FIG. 1. At this time, the needle 18 is withdrawn from the septum 17 while the septum self-seals. Thereafter, the male adapter 27 can be withdrawn from the female adaptor 14 or retained in place for a subsequent infusion of medicament.

The connector 10 may initially have a dust cap (not shown) mounted over the adaptor 14 in order to maintain the chamber 16 in a sterile condition. The sterility of the IV line is assured by the rubber septum 17 being closed and the collapsible means 20 about the needle 18 being completely closed.

The connector or luer fitting 27 of the syringe 28 may be wiped with an antiseptic material prior to insertion into the adapter 14 of the connector 10 in order to remove any trace of contamination prior to hook-up.

Figure 3:
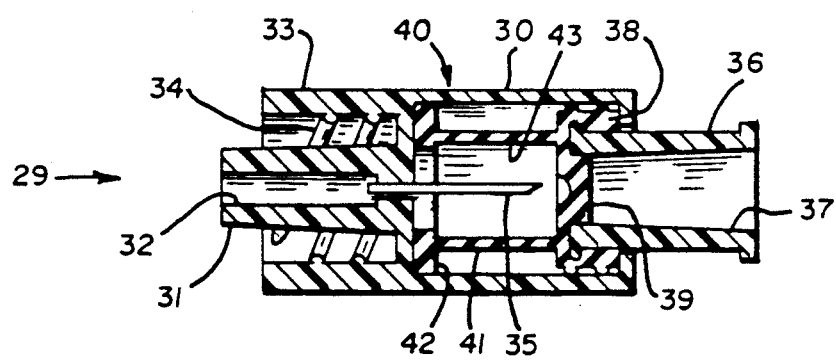
FIG. 3 illustrates a cross sectional view of a modified connector constructed in accordance with the invention.

Referring to FIG. 3, the connector 29 is formed of a housing 30 having a male luer connection 31 defining a flow path 32 for fluid. As indicated, the housing 30 has a cylindrical extension 33 disposed in coaxial spaced relation to the luer connection 31 so as to define an annular gap. In addition, the extension 33 has a helical thread 34 on the inside wall for purposes as explained below.

The connector 29 also has a hollow needle 35 mounted in the housing 30 coaxially of the male connection 31 with a proximal end of the needle 35 opening into the flow path 32 of the connection 31.

A female adaptor 36 in the form of a female luer connector is slidably mounted in the housing 30 coaxially of the needle 35 and defines an internal chamber 37 for receiving fluid. In addition, an annular sealing ring 38 having a pair of annular sealing surfaces is disposed between the housing 30 and the adapter 36 to maintain a sealed condition between the adaptor 36 and housing 30.

A rubber septum 39 is disposed in sealed relation between the adaptor 36 and the needle 35. As illustrated, the septum 39 has a reduced portion opposite the distal end of the needle 35 for piercing thereby.

Figure 4:
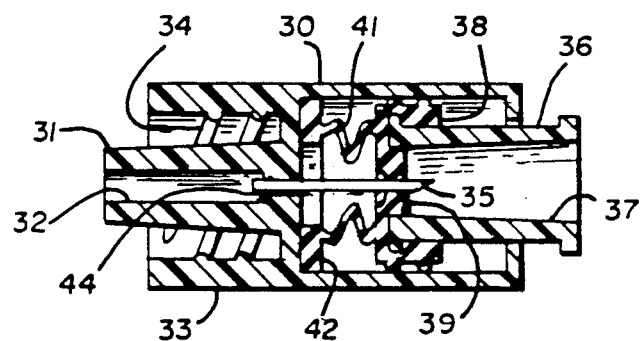
FIG. 4 illustrates a cross sectional view of the connector of FIG. 3 in a collapsed state of the collapsible means.

A collapsible means 40 is disposed about the needle 35 between the housing 30 and the adaptor 36. As above, the collapsible means 40 is collapsible into a position as shown in FIG. 4, so as to permit the needle 35 to pierce through the septum 39 into communication with the chamber 37 during movement of the adaptor 36 into the housing 30. As indicated, the collapsible means 40 includes a collapsible cylindrical wall 41 spaced concentrically about the needle 35 and made integral with the septum 39 at one end to seal off the needle 35 from the outside environment. In addition, an annular flange 42 is provided at the opposite end of the wall 41 in sealed relation with the housing 30.

The cylindrical wall 41 defines a chamber 43 in which the needle 35 is initially positioned. In addition, a fluid bypass 44 is provided between the housing 30 and the needle 35 in order to communicate the chamber 43 with the flow path 32 of the male connector 31. Thus, during collapsing of the wall 41, for example, into the position shown in FIG. 4, any fluid within the chamber 43 can be expelled through the bypass 44 into the flow path 42.

In use, the connector 29 is initially connected to, for example, a catheter. Thereafter, a male adaptor, for example, of a syringe or luer connection is inserted into the female adaptor 36 and pushed forwardly. At that time, the adaptor 36 slides into the housing 30 while maintaining a sealed relationship. In addition, the needle 35 pierces the septum 39 to communicate with the chamber 37. The fluid which is in the chamber 37 is then able to pass through the needle 35 into the flow path of the male connector 31 as indicated in FIG. 4.

Figure 5:
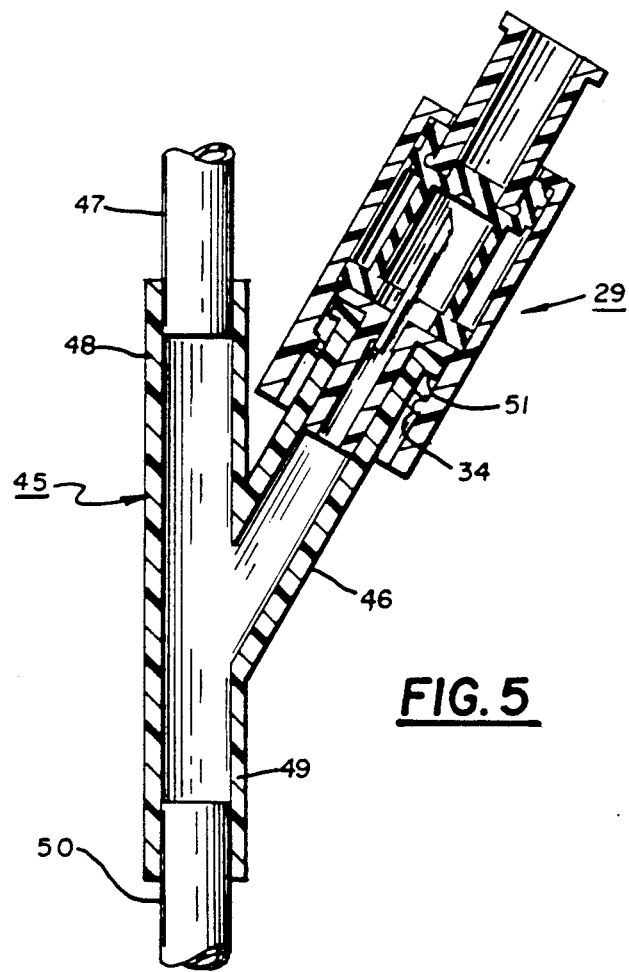
FIG. 5 illustrates a cross sectional view of the connector of FIG. 3 mounted on a Y-site.

Referring to FIG. 5, wherein like reference characters indicate like parts as above, the connector 29 may be mounted on a Y-site 45. As indicated, the Y-site connector 45 has a first inlet branch 48 for connection with an IV tube 47, a second inlet branch 46 on which the connector 29 is mounted and an outlet branch 49 for connection with a catheter tube 50.

The connector 29 is mounted on the inlet branch 46 by a threading on action. In this respect, the inlet branch 46 is provided with a small radially directed flange 51 about which the helical thread 34 of the cylindrical wall 33 of the connector 29 is turned. The thread 34 serves to secure the connector 29 on the inlet branch 46.

After mounting on the Y-site 45, the connector 29 is used in a manner as described above with respect to FIGS. 3 and 4. Thus, a medicament can be introduced through the connector 9 into the Y-site connector 45 from time-to-time for infusion into a bed-ridden patient.

Figure 6:
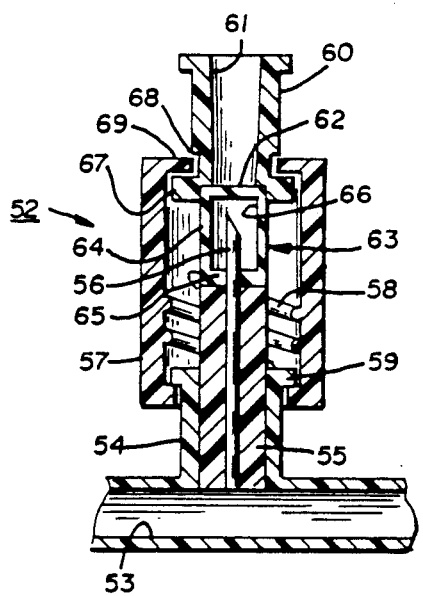
FIG. 6 illustrates a cross sectional view of a further modified connector constructed in accordance with the invention.
Figure 7:
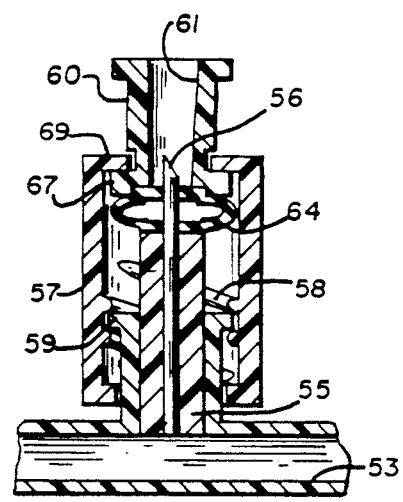
FIG. 7 illustrates a cross sectional view of the connector of FIG. 6 in the collapsed state.

Referring to FIGS. 6 and 7, the connector 52 may be constructed for interconnection with a fluid line. In this respect, the connector 52 has a tube 53 defining a flow path for fluid and a hollow stub 54 extending radially of and in communication with the flow path.

In addition, a holder 55 is mounted in the stub 54 and supports a hollow needle 56 which extends through the holder 55 with a proximal end in communication with the flow path in the tube 53.

A housing 57 is also mounted on the stub 54 concentrically of the holder 55 and the needle 56. As indicated, the housing 57 has an internal helical thread 58 for engaging with a radial flange 59 at the distal end of the stub 54 for engagement purposes.

A female adapter 60 is mounted in and extends from the housing 57 coaxially of the needle 56 and defines an internal chamber 61 for receiving fluid.

A rubber septum 62 is disposed in sealed relation between the adapter 60 and the needle 56. In addition, a collapsible means 63 is disposed about the needle 56 between the holder 55 and the adapter 60. As above, this means is collapsible to permit the needle 56 to pierce through the septum 62 into communication with the chamber 61 during movement of the adaptor 60 towards the needle 56. As indicated, the collapsible means 63 includes a collapsible cylindrical wall 64 spaced concentrically about the needle 56 which is integral with the septum 62. In addition, an end wall 65 is disposed at the opposite end of the wall 64 such that the collapsible means 63 defines a closed chamber 66 in which the distal end of the needle 56 is positioned. As indicated, the needle 56 passes through the end wall 65 in sealed relation therewith.

The adaptor 60 is provided with a radial flange 67 and an annular groove 68 adjacent the flange 67 sized to receive an inwardly directed flange 69 of the housing 57. In this way, the housing 57 is secured to the adaptor 60 for movement therewith over the needle holder 55.

The helical rib 58 and corresponding flange 59 of the stub 54 function as a locking means for releasably locking the housing 57 relative to the holder 55 in a collapsed position of the collapsible means 63 as indicated in FIG. 7.

The connector 52 is utilized in a manner similar to the above connectors 10, 29. That is, the tube 53 is first connected into a fluid supply line. Thereafter, a male luer connector or the like can be inserted into the female adaptor 60 so as to deliver fluid into the chamber 61. When this fluid is to be injected into the supply line, the adaptor 60 and interconnected housing 57 are pushed toward the tube 53 so that the distal end of the hollow needle 56 pierces the septum 62 and passes into the chamber 61. At this time, the fluid in the chamber 61 communicates directly via the needle 56 with the flow path of the tube 53. Upon pulling of the adaptor 60 from the tube 53, the collapsed wall 64 moves into the extended position and the hollow needle 56 retracts from the within the chamber 61 while the septum 62 again affects a sealing of the chamber 61.

Figure 8:
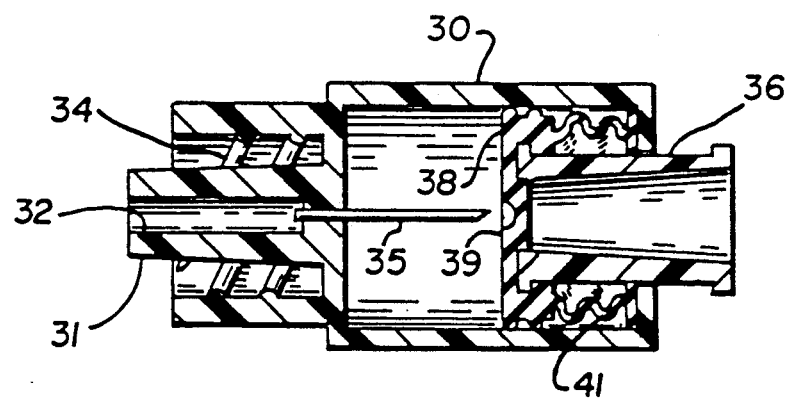
FIG. 8 illustrates a cross-sectional view of a modified connector similar to that of FIG. 3.
Figure 9:
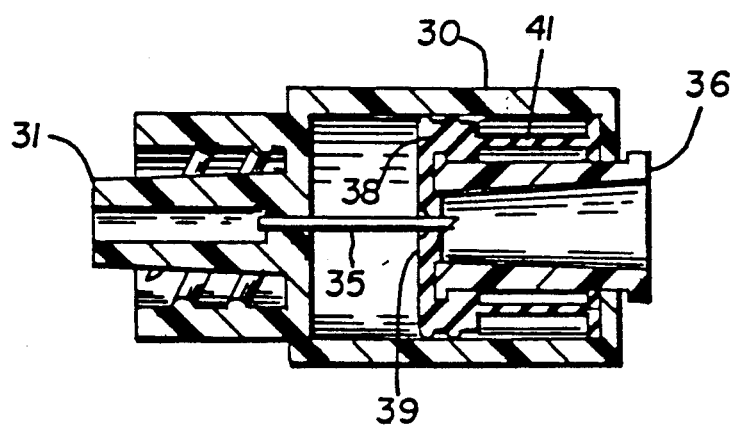
FIG. 9 illustrates a cross-sectional view of the connector of FIG. 8 in a position with a needle piercing a septum.

Referring to FIGS. 8 and 9, wherein like reference characters indicate like parts as above, the cylindrical wall 41 is spaced concentrically about the adaptor 36 between the septum 39 and an end wall of the housing 30. In this variant, the wall 41 is movable from the collapsed position of FIG. 8 to the expanded position of FIG. 9 during movement of the adaptor 36 into the housing 30.

The positioning of the wall 41 about the adaptor 36 provides a double seal. Thsat is, while the seal ring 38 seals off the needle 35 from the environment outside the housing 30, the cylindrical wall 41 maintains the interior of the housing 30 in a sealed aseptic condition.

The invention thus provides a connector in which a hollow needle is self-contained in a sealed manner so as to preclude exposure of the needle.

The invention further provides a connector of relatively simple construction which can be adapted to various fluid transfer systems such as IV lines and Y-sites.

What is claimed is:

1. A connector comprising
   a housing
   a hollow needle mounted in said housing;
   a rubber septum disposed in said housing in facing relation to a distal end of said needle;
   an adaptor extending coaxially of said needle on a side of said septum opposite said needle to define an internal chamber; and
   collapsible means maintaining said needle and said septum in opposed spaced relation relative to each other and being collapsible to permit said needle to pierce through said septum into communication with said chamber during relative movement therebetween.

2. A connector as set forth in claim 1 wherein said collapsible means is secured to said needle for movement therewith relative to said septum.

3. A connector as set forth in claim 1 wherein said collapsible means is integral with said septum for movement therewith relative to said needle.

4. A connector as set forth in claim 1 wherein said housing includes a flow path extending from and in communication with a proximal end of said needle.

5. A connector as set forth in claim 4 wherein said housing includes a male luer connector defining said flow path.

6. A connector as set forth in claim 1 wherein said adaptor is a female luer adaptor.

7. A connector as set forth in claim 1 wherein said housing has a cylindrical portion defining a flow path perpendicular to said needle and said needle has an aperture in a side wall opening into said flow path.

8. A connector comprising
   a housing having a hollow cylindrical portion defining a flow path for fluid and adapted to receive tubing at opposite thereof;
   a female adaptor extending radially of and in communication with said flow path in said cylindrical portion to define an internal chamber;
   a rubber septum in said adaptor separating said chamber from said flow path in said cylindrical portion;
   a hollow needle mounted in said housing in said coaxial relation to said septum, said needle having at least one aperture opening into said flow path of said cylindrical portion; and
   collapsible means disposed on said housing and secured to said needle for movement between an extended position with said needle spaced from said septum and a collapsed position with said needle piercing said septum and extending into said chamber for conveying fluid therefrom into said flow path of said cylindrical portion of said housing.

9. A connector as set forth in claim 8 wherein said collapsible means includes an end wall secured to said needle and a collapsible cylindrical wall spaced concentrically about said needle and secured to said housing.

10. A connector as set forth in claim 8 wherein said housing has a hollow stub opposite said adaptor and in communication with said flow path, and wherein said needle is slidably mounted in said stub in sealed relation therewith.

11. A connector as set forth in claim 10 wherein said housing is made of plastic and said needle is made of metal.

12. A connector comprising
    a housing having a male luer connector defining a flow path for fluid;
    a hollow needle mounted in said housing coaxially of said connector and having a proximal end opening into said flow path of said connector;
    a female adaptor slidably mounted in said housing coaxially of said needle to define an internal chamber;
    a rubber septum disposed in sealed relation between said adaptor and said needle; and
    collapsible means sealingly disposed between said housing and said adaptor and being movable from a first position to a second position to permit said needle to pierce through said septum into communication with said chamber during movement of said adaptor into said housing for conveying fluid from said chamber into said flow path of said male luer connector.

13. A connector as set forth in claim 12 wherein said collapsible means includes a collapsible cylindrical wall spaced concentrically about said needle and within said housing to move from an expanded position to a collapsed position during movement of said adaptor into said housing.

14. A connector as set forth in claim 13 wherein said cylindrical wall is integral with said septum.

15. A connector as set forth in claim 14 wherein said wall defines a second chamber and said housing has a passageway communicating with said second chamber with said flow path of said male luer connection.

16. A connector as set forth in claim 13 which further comprises an annular flange on said wall in sealing relation with said housing.

17. A connector as set forth in claim 12 wherein said collapsible means includes a collapsible cylindrical wall spaced concentrically about said adaptor to move from a collapsed position to an expanded position during movement of said adaptor into said housing.

18. A connector as set forth in claim 12 wherein said housing has a cylindrical wall concentric to and spaced from said male luer connection.

19. A connector as set forth in claim 12 which further comprises a sealing ring between said adaptor and said housing.

20. A connector comprising
    a tube defining a flow path for fluid, said tube having a hollow stub extending radially of and in communication with said flow path;
    a holder mounted in said stub;

a hollow needle extending through said holder with a proximal end in communication with said flow path;

a housing mounted on said stub concentrically with said flow path;

a female adaptor mounted in and extending from said housing coaxially of said needle to define an internal chamber; and a rubber septum disposed in sealed relation between said adaptor and said needle; and collapsible means disposed about said needle between said holder and said adaptor, said means being collapsible to permit said needle to pierce through said septum into communication with said chamber during movement of said adaptor towards said needle for conveying fluid from said chamber into said flow path of said tube.

21. A connector as set forth in claim 20 wherein said collapsible means includes a collapsible cylindrical wall spaced concentrically about said needle.

22. A connector as set forth in claim 21 wherein said wall is integral with said septum and an end wall opposite said septum to define a second chamber, said needle passing through said end wall into said second chamber.

23. A connector as set forth in claim 20 wherein said housing is secured to said adaptor for movement therewith over said needle holder.

24. A connector as set forth in claim 23 which further comprises a locking means for releasably locking said housing relative to said holder in a collapsed position of said collapsible means.

25. A connector as set forth in claim 24 wherein said locking means includes an outwardly directed flange on said holder and a helical internal rib on said housing for releasably holding said flange therebetween.

26. In combination a Y-site connector having a first inlet branch for connection with an IV tube, a second inlet branch and an outlet branch for connection with a catheter tube; and a connector mounted on said second inlet branch, said connector having a housing with a male luer connection at one end mounted in said second inlet branch, a hollow needle having a proximal end in communication with said male luer connection, an adaptor slidably mounted in said housing coaxially of said needle to define an internal chamber, a rubber septum disposed in sealed relation between said adaptor and said needle, and collapsible cylindrical wall disposed between said housing and said adaptor and movalbe from a first position to a second position to permit said needle to pierce through said septum into communication with said chamber during movement of said adaptor into said housing for conveying fluid from said chamber into said flow path of said male luer connector and said second inlet branch.

27. The combination as set forth in claim 26 wherein said adaptor is a female luer connection.

28. A connector as set forth in claim 1 wherein said housing is a one-piece housing and said adaptor is integral with said housing.

29. A connector as set forth in claim 28 wherein said collapsible means is disposed on said housing and secured to said needle for movement between an extended position with said needle spaced from said septum and a collapsed position with said needle piercing said septum.

30. A connector as set forth i claim 29 wherein said housing has a cylindrical portion defining a flow path perpendicular to said adaptor and said needle and wherein said hollow needle has an aperture in a side wall opening into said cylindrical portion.

* * * * *

UNITED STATES PATENT AND TRADEMARK OFFICE
CERTIFICATE OF CORRECTION

PATENT NO. : 4,998,927

DATED : March 12, 1991

INVENTOR(S) : VINCENT L. VAILLANCOURT

It is certified that error appears in the above-identified patent and that said Letters Patent is hereby corrected as shown below:

```
Column 1, line 13 change "a" to -an-
Column 1, line 65 change "with" to -which-
Column 4, line 20 change "6" to -16-
Column 4, line 37 change "12" to -13-
Column 6, line 67 delete "the"
Column 7, line 10 change "Thsat" to -That-
Column 7, line 57 change "opposite" to -opposite ends-
Column 8, line 48 delete "with"
Column 10, line 15 change "movalbe" to -movable-
```

Signed and Sealed this

Sixth Day of October, 1992

Attest:

DOUGLAS B. COMER

*Attesting Officer*  *Acting Commissioner of Patents and Trademarks*